(12) United States Patent
Daffer (10) Patent No.: US 11,311,410 B2
(45) Date of Patent: Apr. 26, 2022

(54) HYPERTHERMIC CONDITIONING CAPSULE

(71) Applicant: Visibelle Derma Institute, Inc., Bloomington, MN (US)

(72) Inventor: Steven J. Daffer, Edina, MN (US)

(73) Assignee: Visibelle Derma Institute, Inc., Bloomington, MN (US)

( * ) Notice: Subject to any disclaimer, the term of this patent is extended or adjusted under 35 U.S.C. 154(b) by 131 days.

(21) Appl. No.: 16/010,927

(22) Filed: Jun. 18, 2018

(65) Prior Publication Data
US 2018/0360649 A1 Dec. 20, 2018

Related U.S. Application Data

(60) Provisional application No. 62/521,802, filed on Jun. 19, 2017.

(51) Int. Cl.
*A61F 7/00* (2006.01)
*A61M 21/00* (2006.01)
(Continued)

(52) U.S. Cl.
CPC .......... *A61F 7/0053* (2013.01); *A61F 7/0085* (2013.01); *A61M 19/00* (2013.01); *A61M 21/0094* (2013.01); *A61N 5/0625* (2013.01); *A63B 21/0023* (2013.01); *A63B 21/0552* (2013.01); *A63B 21/065* (2013.01); *A63B 21/0628* (2015.10); *A63B 21/4013* (2015.10); *A63B 21/4021* (2015.10); *A63B 21/4034* (2015.10); *A63B 21/4035* (2015.10);
(Continued)

(58) Field of Classification Search
USPC .............................................. 607/77; 600/21
See application file for complete search history.

(56) References Cited

U.S. PATENT DOCUMENTS 1,221,163 A 4/1917 Frink
1,643,528 A 9/1927 Thurston
(Continued)

FOREIGN PATENT DOCUMENTS

DE 725804 3/1944
DE 3915008 A1 11/1990
(Continued)

OTHER PUBLICATIONS

Chinese First Correction Notice dated Apr. 8, 2019 for corresponding Chinese Application No. 201820946569.0, filed Jun. 19, 2018.
(Continued)

*Primary Examiner* — Gary Jackson
*Assistant Examiner* — Anant A Gupta
(74) *Attorney, Agent, or Firm* — Peter J. Ims; Westman, Champlin & Koehler, P.A.

(57) ABSTRACT

A self-contained, hyperthermic conditioning unit and selectively controllable environment for exercising. The unit comprises a base portion having a bed therein and a removable cover connected to the base portion to enclose a personal compartment within the unit. One or more heating elements provide heat to the personal compartment and one more pieces of physical exercise equipment are provided within the personal compartment.

17 Claims, 5 Drawing Sheets

(51) Int. Cl.

| | | |
|---|---|---|
| A63B 21/055 | (2006.01) | |
| A63B 22/04 | (2006.01) | |
| A63B 22/06 | (2006.01) | |
| A63B 21/002 | (2006.01) | |
| A63B 21/00 | (2006.01) | |
| A63B 21/065 | (2006.01) | |
| A63B 21/062 | (2006.01) | |
| A61N 5/06 | (2006.01) | |
| A61M 19/00 | (2006.01) | |
| A61N 5/00 | (2006.01) | |
| A61M 11/00 | (2006.01) | |

(52) U.S. Cl.
CPC .......... *A63B 22/04* (2013.01); *A63B 22/0605* (2013.01); *A61F 2007/0052* (2013.01); *A61F 2007/0055* (2013.01); *A61F 2007/0057* (2013.01); *A61F 2007/0086* (2013.01); *A61F 2007/0093* (2013.01); *A61F 2007/0096* (2013.01); *A61M 11/00* (2013.01); *A61M 2021/0027* (2013.01); *A61M 2021/0044* (2013.01); *A61M 2021/0055* (2013.01); *A61M 2021/0066* (2013.01); *A61M 2021/0072* (2013.01); *A61M 2202/0208* (2013.01); *A61M 2205/051* (2013.01); *A61M 2205/056* (2013.01); *A61M 2205/3368* (2013.01); *A61M 2205/3606* (2013.01); *A61M 2205/368* (2013.01); *A61M 2205/3646* (2013.01); *A61M 2230/06* (2013.01); *A61M 2230/205* (2013.01); *A61M 2230/30* (2013.01); *A61M 2230/50* (2013.01); *A61N 2005/007* (2013.01); *A61N 2005/0637* (2013.01); *A61N 2005/0652* (2013.01); *A61N 2005/0659* (2013.01); *A63B 2208/0252* (2013.01); *A63B 2213/002* (2013.01); *A63B 2213/005* (2013.01)

(56) References Cited

U.S. PATENT DOCUMENTS

| | | | |
|---|---|---|---|
| 1,797,916 A | | 3/1931 | Kruse |
| 2,012,221 A | | 8/1935 | Clark et al. |
| 2,096,128 A | | 10/1937 | Mortrude, Jr. |
| 2,240,819 A | | 5/1941 | Waly |
| 2,300,455 A | | 11/1942 | Lukats |
| 2,567,614 A | | 9/1951 | Merriam |
| D189,951 S | | 3/1961 | Cosper |
| 3,409,915 A | * | 11/1968 | Gregoire ............... B25C 3/006 4/528 |
| 3,772,713 A | | 11/1973 | Roullier |
| 3,945,058 A | | 3/1976 | Gardner |
| 4,031,573 A | | 6/1977 | Romanoff |
| 4,055,863 A | | 11/1977 | Duval |
| D249,894 S | | 10/1978 | Brancaccio et al. |
| 4,130,120 A | | 12/1978 | Kohler, Jr. |
| D255,491 S | | 6/1980 | Brancaccio et al. |
| 4,258,706 A | | 3/1981 | Shank |
| 4,277,855 A | | 7/1981 | Poss |
| 4,389,066 A | * | 6/1983 | Weir ..................... A61G 1/007 280/19.1 |
| D275,605 S | | 9/1984 | Taylor |
| 4,565,188 A | | 1/1986 | Hardie |
| 4,671,284 A | | 6/1987 | Wilson et al. |
| 4,712,538 A | | 12/1987 | Hardie et al. |
| D297,863 S | | 9/1988 | Hardie et al. |
| 4,833,739 A | | 5/1989 | Sakakibara et al. |
| 4,862,526 A | | 9/1989 | Berger |
| 4,884,574 A | | 12/1989 | Hardie et al. |
| D317,650 S | | 6/1991 | Soder |
| 5,101,809 A | * | 4/1992 | Daffer ............... A61H 15/0078 4/529 |
| D326,720 S | | 6/1992 | Garrison et al. |
| 5,228,150 A | | 7/1993 | Parker |
| 5,255,399 A | | 10/1993 | Park |
| D340,992 S | | 11/1993 | Garrison |
| 5,416,931 A | | 5/1995 | Wolfenden et al. |
| D360,469 S | | 7/1995 | Panelli |
| 5,441,529 A | | 8/1995 | Dorsch |
| 5,511,254 A | | 4/1996 | O'Brien |
| 5,546,678 A | | 8/1996 | Dhaemers |
| D377,530 S | | 1/1997 | Daffer et al. |
| 5,645,578 A | | 7/1997 | Daffer et al. |
| D384,416 S | | 9/1997 | Daffer et al. |
| 5,891,186 A | * | 4/1999 | Daffer ................... A61N 5/06 607/91 |
| D413,388 S | | 8/1999 | Daffer et al. |
| 6,004,344 A | | 12/1999 | Fujii |
| 6,066,087 A | * | 5/2000 | Tron ..................... A61H 33/06 600/21 |
| D453,834 S | | 2/2002 | Daffer et al. |
| 6,350,275 B1 | | 2/2002 | Vreman et al. |
| 6,497,717 B1 | * | 12/2002 | Daffer ................... A61F 7/0053 607/81 |
| 6,623,511 B1 | * | 9/2003 | Daffer ................... A61F 7/0053 128/898 |
| 7,282,060 B2 | | 10/2007 | DeBenedictis et al. |
| 7,461,797 B2 | * | 12/2008 | Bhat ..................... B05B 1/005 239/455 |
| 7,526,344 B2 | | 4/2009 | Kim |
| 9,808,644 B2 | | 11/2017 | Daffer |
| 10,744,340 B2 | | 8/2020 | Daffer |
| 2002/0198575 A1 | | 12/2002 | Sullivan |
| 2003/0089370 A1 | * | 5/2003 | Daffer ................... A61H 35/00 128/201.24 |
| 2006/0200211 A1 | | 9/2006 | Lin |
| 2006/0253175 A1 | | 11/2006 | Fan et al. |
| 2007/0282400 A1 | | 12/2007 | Gorham |
| 2009/0222070 A1 | * | 9/2009 | Daffer ................... A61N 5/0613 607/91 |
| 2010/0049282 A1 | | 2/2010 | Wang |
| 2010/0063487 A1 | | 3/2010 | Straalen |
| 2020/0330787 A1 | | 10/2020 | Daffer |

FOREIGN PATENT DOCUMENTS

| | | |
|---|---|---|
| EP | 0986985 A1 | 3/2000 |
| FR | 2086905 A5 | 12/1971 |
| FR | 2629343 A1 | 10/1989 |
| FR | 2803512 A1 | 7/2001 |
| GB | 1490381 | 11/1977 |
| JP | 8112302 A | 5/1996 |
| JP | 11114008 A | 4/1999 |
| WO | 0002491 A1 | 1/2000 |
| WO | 03034971 A2 | 5/2003 |

OTHER PUBLICATIONS

Prosecution History from U.S. Appl. No. 12/396,847, filed Mar. 3, 2009 including: Notice of Allowance and Fee(s) Due dated Sep. 5, 2017, Non-Final Rejection dated Nov. 21, 2016, Final Rejection dated Oct. 6, 2014, Non-Final Rejection dated Dec. 23, 2013, Final Rejection dated Feb. 9, 2012, and Non-Final Rejection dated Aug. 4, 2011.

Prosecution History from U.S. Appl. No. 15/796,141, filed Oct. 27, 2017 including: Notice of Allowance and Fee(s) Due dated Apr. 9, 2020 and Non-Final Rejection dated Dec. 23, 2019.

* cited by examiner

HYPERTHERMIC CONDITIONING CAPSULE

CROSS-REFERENCE TO RELATED APPLICATIONS

The present application is based on and claims the benefit of U.S. provisional patent application Serial No. 62/521,802, filed Jun. 19, 2017, the content of which is hereby incorporated by reference in its entirety.

BACKGROUND

The present disclosure relates to an individual capsule in which a person can lie in for various treatments. The capsule includes the ability to provide a hyperthermic conditioning environment by providing a heated capsule. The capsule may have exercise equipment therein for use in a temperature controlled environment.

In the prior art, various environmental capsules have been advanced, including for example, the structure shown in U.S. Pat. No. 5,101,809 and U.S. Pat. No. 6,497,717. The treatments that are present in the prior art devices include steam therapy, heat therapy, infrared heat and light exposure, pleasing sound sources, aroma therapy and some capsules provide a shower mounted in the cover or base of the capsule.

The capsules generally have a base that is large enough to accommodate a support or bed in a lower portion, and a hinged cover that can be opened so that a person can get in and out of the lower part or base of the capsule. The cover usually has individual controls to provide therapy source such as a shower, heat, steam, sound, aroma or other therapy source can be mounted in a position where a person lying on the bed can reach and operate the controls. In addition, it has long been known to have a vibrator on the bed to provide a relaxing, massage type vibration.

SUMMARY

The present disclosure relates to a self-contained, personal exercise unit where conditions such as temperature can be selectively controlled to provide one or more controllable environments within the unit. The unit is configured for providing a controlled hyperthermic conditioning environment and/or optionally a controlled hypothermic conditioning environment. The unit includes a capsule configured to provide two independently controllable environments. The capsule includes an upper body (i.e. head/neck and in some cases the upper shoulders) area which is selectively enclosable and an internal bed component adapted with various physical exercise equipment for use by a human user within the capsule. The capsule includes sources of heat including a heater and LED and/or infrared lighting and/or cooling, such as an air conditioner. The capsule may also optionally include one or more shower heads, air control, light, steam, and/or misting spray devices to provide complimentary conditions for the human user before, during or after exercise in the capsule. This is in addition to the hyperthermic conditioning environment and optionally the hypothermic conditioning environment.

The personal capsule includes a base supporting a bed and has a movable cover adapted with a pop-up translucent hood and dome. The cover, and hood and dome are selectively closeable to separate an upper body, or head chamber from a main body chamber, wherein an environment of both chambers is selectively controllable. The main body chamber comprises the bed, which may be a fitness or exercise bed configured to receive a person lying down and adapted with connections for various exercise equipment such that the user is able to utilize the exercise equipment within the bed and thus within the capsule. The various exercise equipment may be positioned in, on, or around the perimeter of the bed at selected locations appropriate for the specific use of the equipment by the user. For example, the individual pieces of exercise equipment are positioned within reach of the user's hands or feet within the capsule.

The movable cover and pop-up hood and dome are configured to allow the upper body area and the main body area to be one continuous chamber having a selectively controllable environment, or to be two individual and adjacent chambers, each having a separately controllable environment. The bed and cover combine to provide a personal compartment having a controllable internal environment, where for example, the temperature and humidity of the environment can be selected and controlled to provide a controllable hyperthermic or hypothermic conditioning environment for the user. However, the capsule allows the user to select a single (the same) environment for their entire body or select an environment for their head and face that is different than the environment for the user's body. For example, misting may be including one or both chambers and/or the chambers may have varying humidity levels or temperatures.

The capsule is of dimensions sufficiently large to allow the user to move within the personal compartment when utilizing the various exercise equipment therein or partially therein.

Infrared heaters or dry heat sources are also be provided along the internal sides of the cover to direct heat onto the person lying on the bed.

Exercise resistance bands are also provided and are attached along the sides of the bed. The resistance bands can be utilized to provide resistance training and physical exercise to the person within the capsule. The bands can be used when heat is directed down onto the person lying on the bed, and/or when the temperature of the compartment is elevated.

The device may include a stack of weights that are coupled to hand or foot grips with a cable. The stack of weights allow for resistant weight training within the thermally controlled environment. The stack of weight can be located within the capsule or external to the capsule while the hand or foot grips are located within the capsule.

A push pedal stepper system or a stationary cycle may also be provided and attached to the foot area of the bed. The push pedal stepper system or the stationary cycle can be utilized to provide resistance movement and physical exercise to the lower body and legs of the person within the capsule. The stepper system or the stationery cycle can be used when heat or cooling is directed down onto the person lying on the bed, and/or when the temperature of the compartment is elevated or depressed.

Hand stirrups or other handles may also be provided and attached along the sides of the bed. The hand stirrups can be utilized to provide isometric exercise options, including allowing the person within the capsule and lying in the bed to do stomach crunches, core workouts, sit-up, pull-ups and/or shoulder shrugs. The hand stirrups can be used when heat or cooling is directed onto the person lying on the bed, and/or when the temperature of the compartment is elevated.

A removable pull up bar may also be provided and attached over the open hood area of the cover. The pull up bar allows the person within the capsule to do upper body strength exercises such as pull-ups, curls and/or other strength training. The pull up bar can be used when heat is directed down onto the person lying on the bed, and/or when the temperature of the compartment is elevated.

Directed air flow is also provided near the shoulder portion of the bed area for preventing heat loss in the personal compartment when the user selects to open, or pop up, the hood and dome portion of the cover. This allows the conditions within the personal compartment to be controlled or substantially maintained while allowing the user to expose their head and face to the outside or ambient environment.

Additional exercise equipment such as, but not limited to, stretching bands and/or cords, free weights and/or wrist or ankle weights may also be provided in the bed portion.

DETAILED DESCRIPTION

Figure 1:
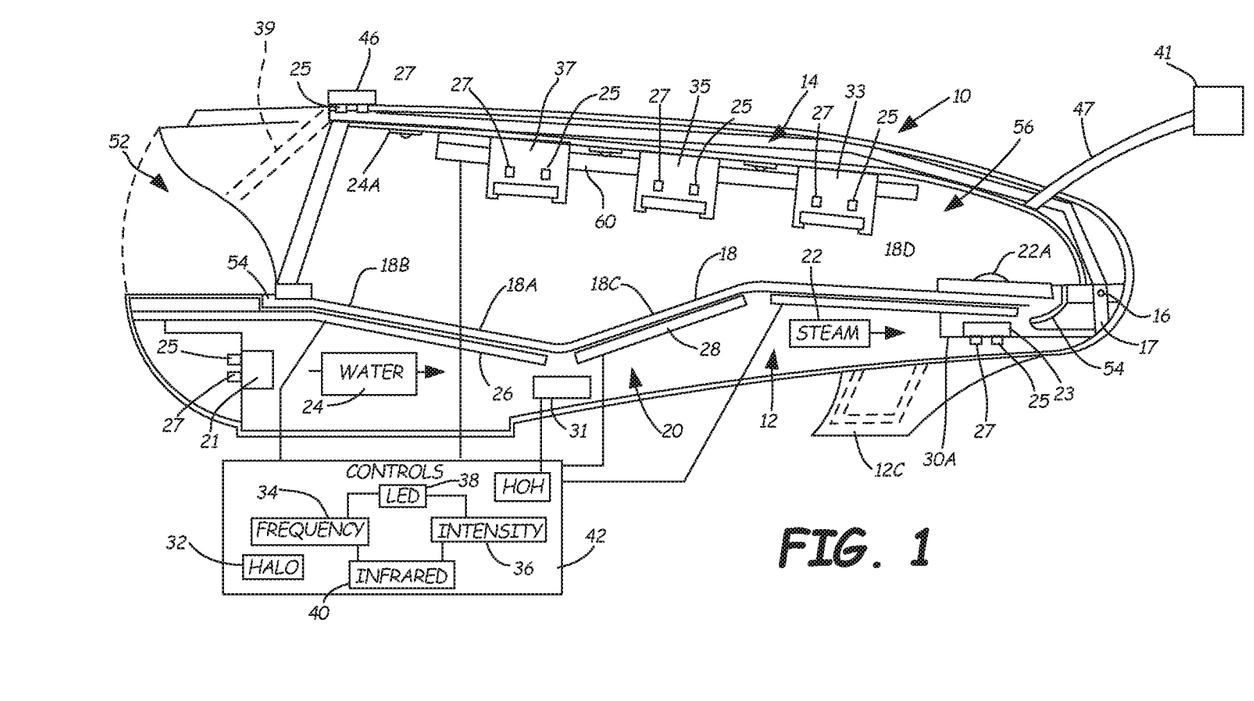
FIG. 1 is a sectional view of a conditioning capsule with a hood in a closed position.
Figure 2:
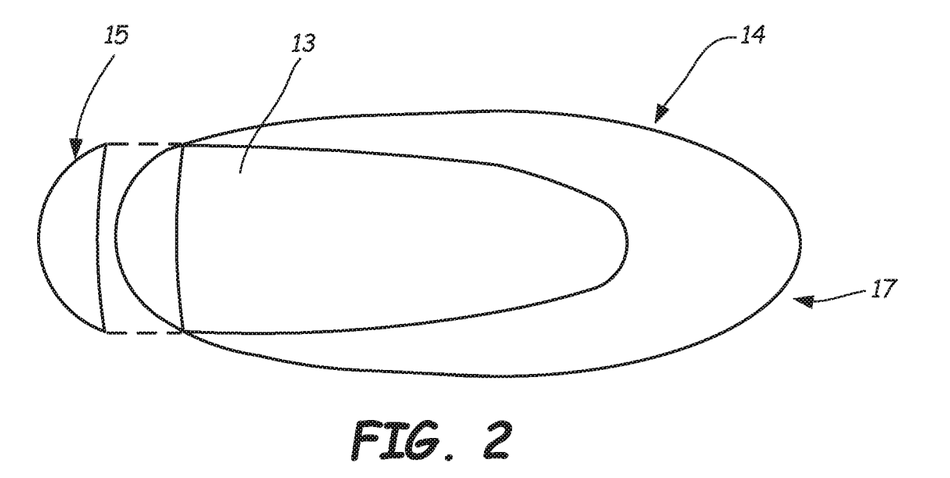
FIG. 2 is a bottom view of the capsule.

A conditioning unit 10 is illustrated generally in the figures. Referring to FIG. 1, a full body compartment assembly is generated at 10 in cross-section, to show an interior cavity 11 of the conditioning unit 10. The conditioning unit 10 includes a base compartment 12 and a cover 14. The cover 14 is operably secured to the base compartment 12 by a hinged connection at a hinge axis 16. The hinge axis 16 can be positioned at the foot end 17 of the base compartment 12. Alternatively, the hinge axis 16 can be positioned along a side length of the base compartment 12. The base compartment 12 is supported on a leg system, such as a three-point leg system preferably including a pedestal 12A, and forward legs 12C as illustrated in FIG. 2.

The three-legged arrangement provides stability of support without rocking or problems with unevenness of a support floor. Other forms of support for the base can be utilized and are contemplated.

The base 12 is provided with a bed 18 therein which can be constructed of a clear acrylic or other clear plastic material, so that it may be transparent to light of different wavelengths. Upper surfaces 18A of the bed 18 are positioned at various angles and the bed 18 includes an upper body portion 18B that supports the shoulder and upper back region of a person lying on the bed 18. The bed 18 also includes a lower back panel or portion 18C, that is at a comfortable angle relative to the upper body portion 18B, and a leg panel or support 18D that is at the foot end 17 of the bed 18.

Schematically represented at 54 are brackets for holding the bed panel 18 in position relative to the base 12. These mounts can be of any desired type.

The base compartment 12 includes a lower compartment 20 that can house various components for selecting the environment conditions within the unit 10. The lower compartment 20 can operably house components including but not limited to a steam generator 22 that is mounted to provide for steam therapy, if desired, through steam outlets represented generally at 22A. The compartment 20 also can hold a water tank 24 having a pump and supply lines connected to showerheads 24A. By way of example, a showerhead 24A is shown in the cover 14 in FIG. 1. The showing of the shower head is not limited to any particular placement. If desired, showerheads can be placed in other locations along the sides of the cover or in the base. Suitable drainage troughs will be provided and this can easily be done because the base 12 is made generally of molded plastic or fiberglass material that can be shaped as desired.

The lower compartment 20 may also house a plurality of salt blocks 21. Additional salt blocks 21 may be positioned on an inner surface of the cover 14. Each block 21 will have corresponding LED clusters 25 and infrared bulbs 27 to provide supplemental energy to the salt blocks in addition to heat provided by a heater 31.

The base 12, bed 18 and cover 14 form an open interior space referred to as a personal compartment 11. The bed 18 is a user platform within the personal compartment 11. The personal compartment 11 is configured to receive a human user and to allow the user to lie on the bed 18 while also allowing sufficient space for the user to move, such as sit up, move arms and/or legs within the personal compartment when utilizing various physical exercise equipment.

The personal compartment 11 is temperature controlled and is thus a heated or cooled personal compartment 11. What is meant by hyperthermic in this disclosure is that hot air can be introduced to the compartment 11 to elevate the temperature within the compartment, thus elevating the body temperature of the user therein. Conversely, what is meant by hypothermic in this disclosure is that cool air can be introduced into the compartment 11 to reduce the temperature within the compartment 11, thus lowering the body temperature of the user therein.

The personal compartment 11 is configured to provide a first controlled environment, which substantially covers the user's main body (for example, depending on user size, covering shoulders to feet) and is also referred to as a body chamber 56. The personal compartment 11 incorporates various fitness and rehabilitation exercise apparatuses, and/or electrical exercise stimulation devices, inside the controllable temperature body chamber 56. As discussed herein, the temperature may be elevated or reduced (cooled chamber) for relief or various therapies and the temperature may be manipulated and controlled by convection, radiance or conduction means.

Figure 3:
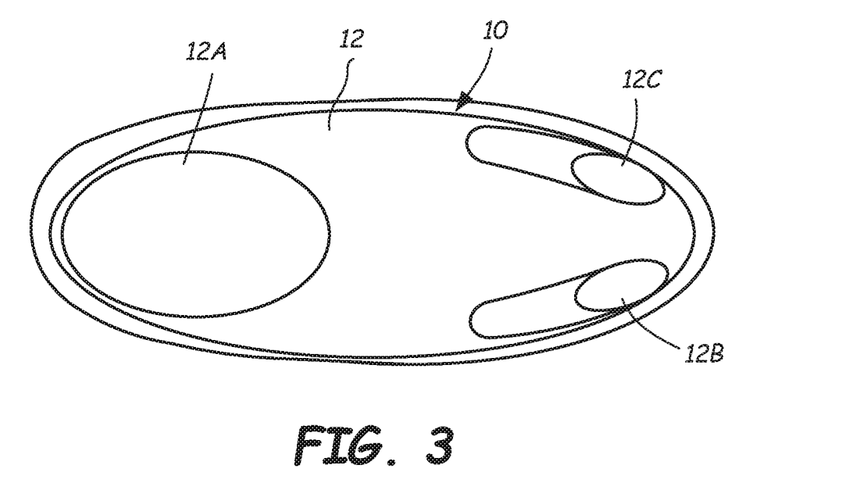
FIG. 3 is a top view of the capsule with the hood in the closed position.
Figure 4:
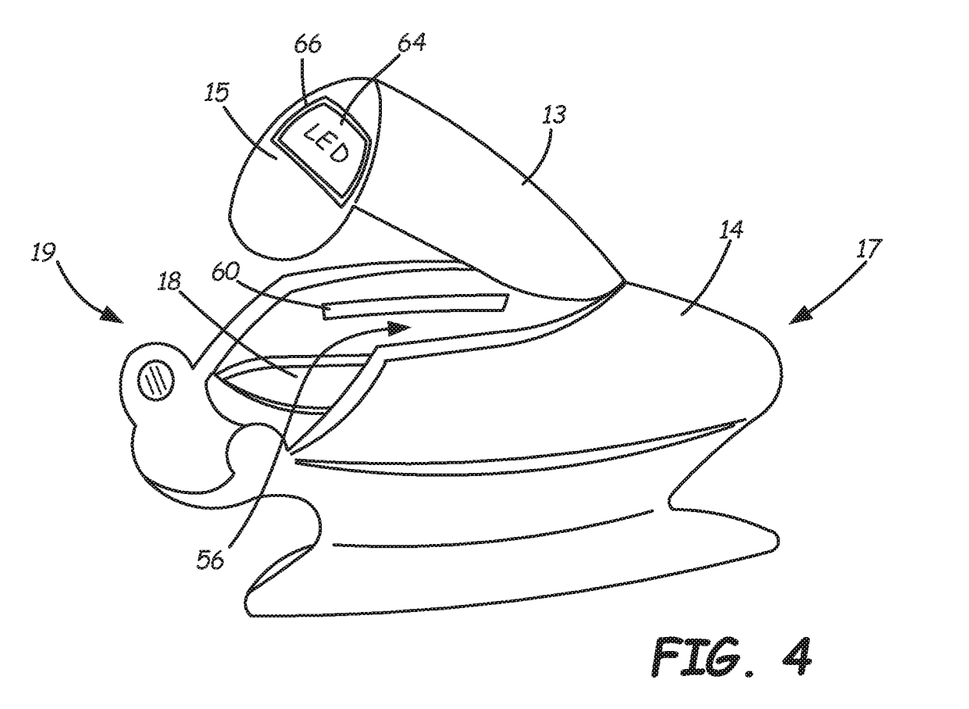
FIG. 4 is a side perspective view of the capsule with an open hood section.
Figure 5:
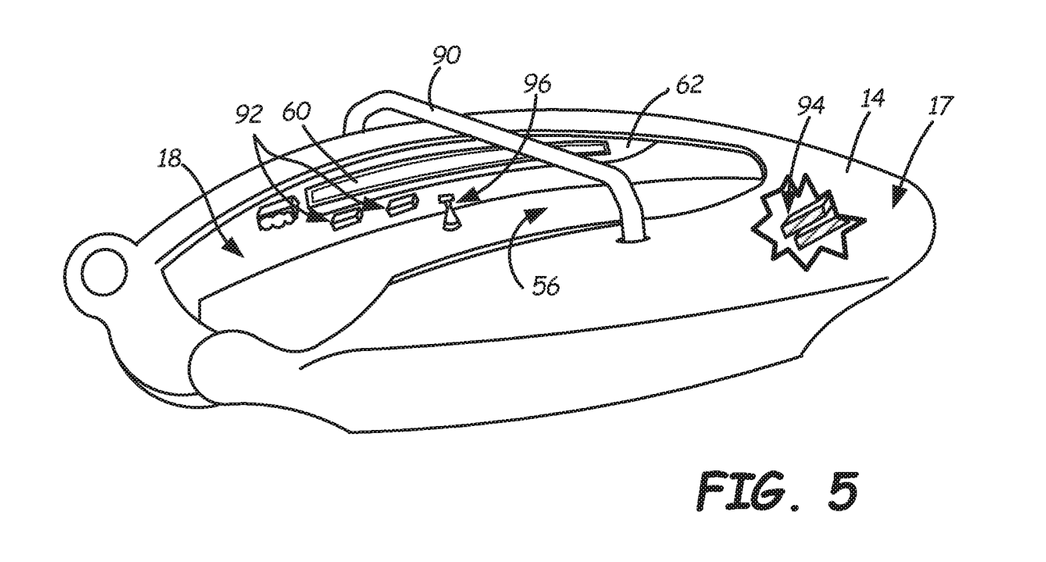
FIG. 5 is a side perspective view of a bed and cover portion of the capsule in an open position where the hood and dome section are removed.

As illustrated in FIGS. 3-5, the cover 14 can be further adapted with a pop-up hood 13 and dome 15. The dome 15 may be made of a translucent or transparent acrylic or other plastic material. The hood 13 and dome 15 are removable, but when in use are portions that extend along a width and a length of an opening in the upper surface of the cover 14. The dome 15 is positioned near the head end 19 of the capsule with the hood 13 extending from the dome 15 towards the foot end 17 of the capsule. The hood 13 can be pivotally connected to the cover 14 at one or more points along the opening or can otherwise be removable and selectively secured to enclose the capsule and the personal compartment 11.

The hood 13 allows the user to open an upper portion 50 of the cover 14 to further open up or enlarge the personal compartment 11. The dome 15, which is also removably secured to the head end 19 of the hood 13 and/or cover 14 is further removable to allow the user to select whether their head and face is covered within the personal compartment 11 or uncovered and exposed to the ambient environment.

The hood 13 and dome 15 may also provide a separate head chamber 52 to the personal compartment 11. As the face of the user (head and neck) generally extends beyond or outside of the open interior space that is the body chamber 56 of the personal compartment 11, the hood 13 and dome 15 are configured to enclose the upper portion 50 as a second separate personal compartment also referred to as the head chamber 52. The head chamber 52 is also configured such that the user can selectively control the environment in the head chamber 52, including for example humidity and temperature.

The dome 15 is closeable to thereby isolate the upper portion 50 from the main body of the personal compartment 11. Thus, the upper portion 50, or head chamber 52, can also be environmentally controlled for temperature (hot or cold) by any temperature control methods described herein or otherwise capable of heating and/or cooling the capsule. Further, the head chamber 52 is also configured with controllable air content (hypo or hyper enriched oxygen, aromas, medical gases, etc.). The environment of the head chamber 52 may be configured with combinations of controllable features also including, but not limited to, humidity, light control or electrical impulse stimulation and/or media stimulation, all of which can be controlled independently from the same or similar controllable features of the body chamber 56 of the personal compartment 11.

As illustrated in FIGS. 4 and 5, removal of the hood 13 allows the upper portion 50 of cover 14 to be opened for additional exercise space. For example, a removable pull up bar 90 may be secured to the capsule cover 14. The removable pull up bar 90 extends across the upper portion 50 of the cover 14, allowing the user additional space and access to the pull up bar 90 from within the personal compartment. The removable pull up bar 90 may be provided and attached over the open area of the upper portion 50 by way of suitable fasteners. Examples of suitable fasteners include but are not limited to bolts, hooks and/or clamps. The pull up bar 90 allows the person within the capsule to perform upper body strength exercises such as pull-ups, curl ups and/or other strength training. The pull up bar 90 can be used when heat is directed down onto the person lying on the bed 18, and/or when the temperature of the compartment is elevated.

Figure 6:
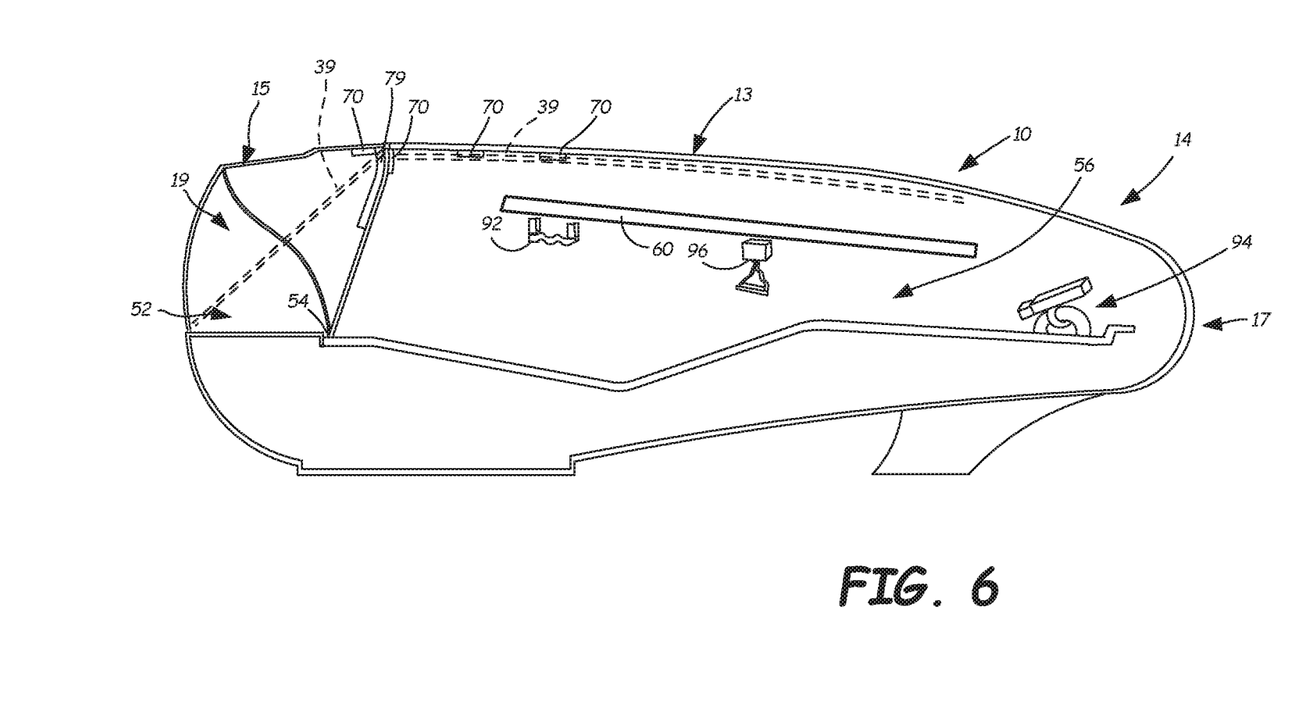
FIG. 6 is a simplified sectional view of the conditioning capsule in a closed view to show conditioning equipment within the capsule.

As illustrated in FIG. 6, various types of exercise equipment, such as resistance equipment such as a recumbent stationary cycling device and/or weights may be installed along the bed 18 and/or inner surface of the cover 14 to provide the personal compartment 11 with exercise equipment therein.

One or more exercise resistance bands 92 are also provided and are attached along the sides of the bed within the capsule. The one or more bands 92 may be usably secured to the sides of the bed, or alternatively to the inside surface of the cover 14. The bed 18 and/or cover 14 are configured for securely receiving the bands 92 in one or more spaces adapted for securing the bands 92 to the bed 18 and/or cover 14 by way of suitable fasteners, examples of which include but are not limited to, bolts, hooks, carabiners, or clamps. The bands 92 are positioned such that a user within the capsule may access, reach and use the bands for stretching and/or strength training. The bands 92 can be used when heat is directed down onto the person lying on the bed 18, and/or when the temperature of the compartment is elevated and/or maintained.

A push-pedal stepper system 94 may also be provided in the foot end 17 of the bed 18. The bed 18 is configured with a space for securably receiving a push-pedal stepper system 94 generally indicated in FIGS. 5 and 6, the stepper system 94 may be usably secured using one or more suitable fasteners or clamps in the foot end 17 of the bed 18. The push-pedal stepper system 94 can be utilized to provide resistance movement and physical exercise to the lower body and legs of the person within the capsule. The stepper system 94 is usably secured to the bed 18 and is oriented for use when the user is sitting or lying down. That is, the stepper system 94 can be used when the personal compartment is enclosed, the hood 13 is secured to the cover 14 or when the compartment is opened removing the hood 13 and dome 15. The stepper system 94 can be used when heat is directed down onto the person lying on the bed 18, and/or when the temperature of the compartment 11 is elevated and/or maintained.

Hand stirrups 96 or other handles may also be provided and usably secured along both sides of the bed 18 or along the inner surface of the cover 14. The bed 18 and/or cover 14 are configured for securely receiving hand stirrups 96 or other handles by way of suitable fasteners, examples of which include but are not limited to, bolts, hooks, carabiners, or clamps The hand stirrups 96 can be utilized to provide isometric exercise options, including allowing the person within the capsule and lying in the bed to do stomach crunches, core workouts, sit-up, pull-ups and/or shoulder shrugs. The hand stirrups can be used when heat is directed down onto the person lying on the bed, and/or when the temperature of the compartment is elevated.

The capsule may also include a system configured for feedback monitoring. Appropriate sensors may be incorporated into either the head chamber 52, the body chamber 56 or both to sense user conditions including, but not limited to, heart rate, blood oxygen content, blood pressure, body temperature, chamber temperature and/or chamber atmospheric content. Further sensors may also be incorporated to monitor and provide exercise apparatus feedback such as reps, resistance, pounds and/or range of motion. The individual sensors may be in wired or wireless connection with a monitor and/or display system positioned adjacent to or outside of the chamber or in or on display panels near the upper portion 50 of the capsule.

Referring back to FIG. 1, the cover 14 is shown as supporting a light panel assembly 60 on the upper portions of the cover 14 in a suitable manner, and which contains myriad of LEDs or infrared lights forming light arrays. The light arrays may be tailored for providing colored lights and/or heating the personal compartment of the capsule.

A tunnel member 62 has light panels positioned along its length. If desired, the tunnel member 62 can carry heated air. An array 60 of LEDs or other lights extends along one or both side lengths of the cover such that the length and width of the LED panel can be made as desired and then supported on the interior upper sides of the cover 14. The infrared light sources can be small bulbs arranged in an array, or larger forms as desired. Infrared light arrays for heat therapy may be directed along the shoulders, along the buttock or back portions, or other areas of the bed as positioned within the capsule.

The cover 14 not only also supports the removable hood 13 and dome 15, but may also support showerheads and/or steam outlets 24A. Steam outlets 24A are illustrated at the forward end of the unit and these can be placed at any desired location. The dome 15 has a panel 64 provided at the head end 19, and this includes the region 66 for supporting a control panel display for the controls shown schematically at 42. The bed 18 provides a recessed area at 68 to permit the neck of the person lying in the compartment to cross the bed 18 so the user's head is positioned under the optional dome 15 and thus to the exterior of the personal compartment.

The capsule also includes an air stream 39 that forces air onto the person's face when within the personal compartment 11 and when the dome 15 is positioned on the cover 14 to enclose the user. Also, oxygen can be injected into the capsule to raise the oxygen concentration within the personal compartment 11.

A water tank 24 can be used for providing a humidifying vaporization and/or misting system through the outlets shown at 24. This system can also be used to allow the application and spray or envelopment of the body of the user of different solutions that are photosensitive and/or photoactive for different therapies. Photosensitive agents can be placed in the tank 24 and then misted onto the body of a person on the bed at desired times.

A facial panel 79 supports an array of a plurality of LEDs. This facial panel 79 can be suspended on or from the hood 13 or dome 15, or adjacent the panel 64. The facial panel 79 can also include adjustable LEDs, of various colors as outlined, and can include infrared lights as well.

Further, directed air provides a curtain along the opening of the cover 14 where the hood 13 and dome 15 are removed. Directed air, by way of air knives or other vents 70 allows for maintaining conditions within the bed 18 when the hood 13 and/or dome 15 is removed or open such that the user's head and face and/or upper body are exposed (for example, the hood 13 and dome 15 are removed when using the removable pull up bar 90). The air flow may be directed by air knives 70 in the sides of the cover proximate the opening and/or other air knives or vents 70 positioned to direct air flow across the neck opening of the personal compartment to prevent significant heat and/or moisture loss in the capsule. The air knives or vents may also be used when the dome 15 is removed but the hood 13 is in use on the cover 14. These air knives are directed to provide a curtain around the user's neck for maintaining the environmental conditions in the otherwise enclosed capsule.

Alternatively, when the cover 14 is positioned on the capsule and the hood 13 and dome 15 are secured on the upper portion 50, the capsule effectively provides two adjacent independently controllable environments. As the user's body extends from the head chamber 52 to the body chamber 56, a panel may extend into the capsule between chambers to further separate the individual environments, where this panel may be configured with a shape to close off the two chambers while allowing the person's neck or shoulders to pass through the area where the two chambers meet. This panel may be comprised of translucent plastic or other lightweight materials to maintain the adjacent independent environments. Additionally, the directed air by way of air knives or other vents 70 also allows for further maintaining of the environments when the hood 13 and dome 15 are closed such that head chamber 52 and body chamber 56 have separate environments that may be independently controlled.

Figure 7:
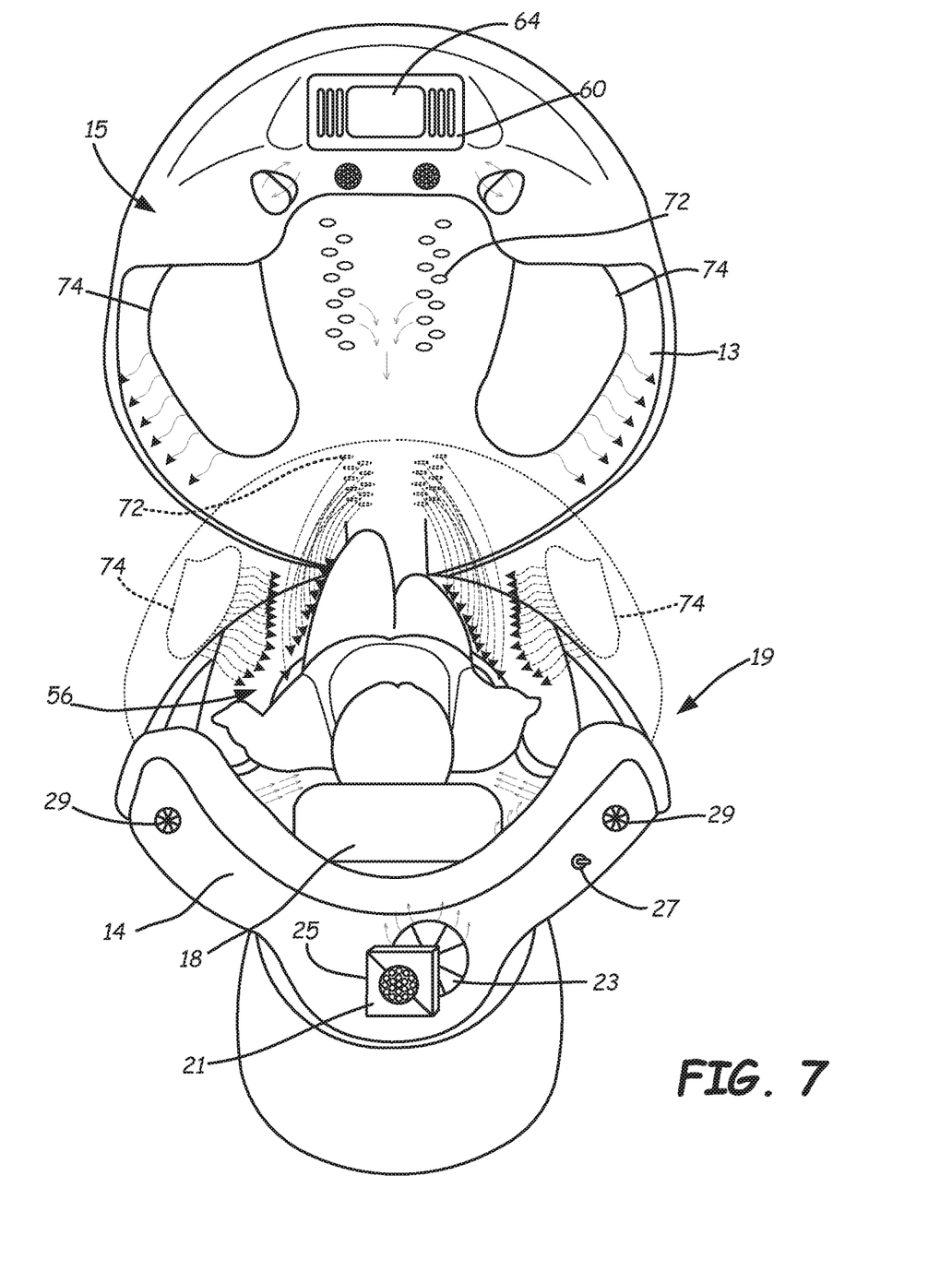
FIG. 7 is a front view of an embodiment of the capsule showing both the cover in an open and closed position.

FIG. 7 illustrates an additional arrangement of elements described herein. The elements described herein can be combined in any manner and elements described in reference to FIGS. 1-6 can be combined with elements or arrangements described in reference to FIG. 7 or vice versa.

FIG. 7 shows the infrared emitters 74 which are positioned on the cover section 14 and provide light therapy and additional controllable heat therapy. The personal compartment 11 can also be equipped with one or more ports 72 which provide dry heat to the body chamber 56 and/or head chamber 52 for controlling the temperature and humidity in the personal compartment 11. The chamber 11 can be heated using convection technology to provide circulating dry heat within the personal compartment 11. Additionally or alternatively, infrared radiation through emitters 74 can be used for heating the personal compartment 11. The personal compartment 11 can be heated in a dual manner.

The personal compartment 11 is further configured controlled environmental conditions by way of one or more cooling fans 29 positioned for directing cooled air towards the head chamber 52 to cool the user's face. Further, purified air can be directed into the personal compartment by a purified fresh air intake fan 23 held in the base 12 or operably secured in the base compartment 20. Pure oxygen can also be provided to the personal compartment 11 or head chamber 52 to assist the user when utilizing exercise equipment in the personal compartment 11.

In addition to providing an environment for hyperthermic conditioning, the capsule 10 can also provide other therapies, such as light therapy. This therapy can be provided by the transparent bed 18 on which a person can lie, in connection with LED lights and infrared light sources comprising small bulbs mounted in an array on a light support panel 26 for the upper back portion of the bed. A light support panel 28 is provided for the lower back, immediately below the lower back panel 18C of the bed, and a pair of leg light panels 30A and 30B are provided (see FIG. 3) that are individually controlled so that one leg or the other or both can be provided with light therapy through the transparent bed which is represented in FIG. 3 by the outline.

In some embodiments, the temperature in the body chamber 56 can be varied by the controller to correspond the temperature with a training routine. For instance, in some routines an elevated temperature body chamber 56 provides beneficial effects as the person exercises. This phenomenon is referred to as hyperthermic training. While the body chamber 56 is at an elevated temperature, the head chamber 52 can be either heated or cooled to provide the desired effects to the head, neck and shoulder region. After the portion of the routine is completed, the person may rest, and the temperature in the body chamber 56 may be lowered to provide cooling.

The temperature of the head chamber 52 can also be adjusted as the temperature of the body chamber 56 is lowered. In some instances, the temperature in the head chamber 52 tracks with the temperature in the body chamber 56. In other instances, the temperature in the head chamber 52 is controlled opposite that of the body chamber 56, meaning if the temperature in the body chamber 56 is elevated, the temperature in the head chamber 52 is suppressed, and vise versa.

In other programs, the temperature in the head chamber 52 and the body chamber 56 track each other, meaning the temperatures rise and fall together. However, the chambers 52 and 56 may be at different temperatures or the same temperature.

In some instances, the body chamber 56 is elevated when the user is exercising to provide hyperthermic conditioning. When the user is not exercising, the temperature in the body chamber 56 may be reduced and is re-elevated as the user exercises. The cycling of the temperature is controlled by a control, where the routine may be preprogrammed or manually controlled by the user.

In other alternatives, hypothermic conditioning may be utilized where cooling is supplied to the body chamber 56 as the user exercises. The head chamber 52 can be cooled or heated, depending upon the desired effect. The user can cycle the temperature for hypothermic conditioning similar to that described with respect to hyperthermic conditioning where the head chamber 52 and the body chamber 56 may be cycled together or inversely.

Additional features such as dry heat air, steam, ceramic and/or course midrange and far-range infrared heaters can be added in the cover. A mist source, a shower, a humidifier, a hydrotherapy source, electrical stimulation and various entertainment sources can be used. Entertainment sources include, without limitation, DVD players, music sources and the like. These features can be selectively applied to either or both the head chamber and the body chamber, separately or concurrently as each of the head chamber and body chamber environments can be independently selected.

Although the present invention has been described with reference to preferred embodiments, workers skilled in the art will recognize that changes may be made in form and detail without departing from the spirit and scope of the invention.

What is claimed is:

1. A self-contained, personal exercise unit configured to provide a selectively controllable environment therein, the unit comprising:
a base portion having a bed component therein and configured to receive a user, the bed component being a user platform secured to the base portion and wherein the user platform is transparent to lights of different wavelengths and wherein surfaces of the bed portion are positioned at various angles such that the bed portion comprises an upper body portion, a lower back portion and a leg panel;
a removable cover hinged connected to the base portion and which provides a substantially enclosed personal compartment within the unit when secured to the base portion and wherein the cover operably supports one or more of a LED light panel, infrared light panel, a source of cooled air, a showerhead, a steam outlet, and a display panel for providing the selectively controllable environment within the substantially enclosed personal compartment;
one or more heating elements configured to provide heat to the personal compartment to selectively control a temperature within the personal compartment;
a removable pull up bar attached to the base and configured for use when the cover is removed; and
one or more pieces of physical exercise equipment secured within the enclosed personal compartment,
wherein the base portion operably supports at least one of the one or more piece of physical exercise equipment operably secured to the bed;
wherein the unit is configured to provide a temperature controlled conditioning environment within the enclosed personal compartment for the user; and
wherein the enclosed personal compartment has dimensions sufficiently large to allow the user to move within the personal compartment when utilizing the one or more pieces of physical exercise equipment operably secured to the bed.

2. The unit of claim 1, wherein the one or more pieces of physical exercise equipment comprise resistance bands, a push pedal stepper system or a stationary cycle, hand stirrups or handles for providing isometric exercise options.

3. The unit of claim 1, wherein the personal compartment is of a size sufficient to allow for the use of exercise equipment selected from the group including stretching bands and/or cords, free weights, and wrist or ankle weights.

4. The unit of claim 1, wherein the personal compartment comprises two independently controllable environments, a first environment surrounding the bed of the unit and the second environment surrounding a user head support area of the bed.

5. The unit of claim 1, wherein the heating elements comprise one or more of a convection heating system and an infrared heating system.

6. A personal hyperthermic conditioning capsule having a base of a size configured to receive a human patient therein, the conditioning capsule configured with two independently controllable chambers to provide one or more selected environments for the human patient therein and the capsule having a plurality of exercise or fitness equipment pieces provided within the capsule and configured for use by the human patient within the capsule, wherein the base comprises a bed and a cover, the cover having a hood and dome, and the cover operably supporting at least two of a heating mechanism, a cooling air source, an infrared light source, an LED light source, a humidity source, and a display screen, and a removable pull up bar attached to the base and configured for use when the cover is removed and the bed being a user platform transparent to one or more wavelengths of light and secured to the base portion and wherein surfaces of the bed portion are positioned at various angles such that the bed portion comprises an upper body portion, a lower back portion and a leg panel and wherein the infrared light source may be targeted to one or more of the upper body portion, lower back portion or leg panel of the bed portion and the bed portion supporting at least two different pieces of physical exercise equipment operably secured thereto and wherein the capsule has dimensions sufficiently large to allow the human patient to move within the capsule when utilizing the at least two different pieces of physical exercise equipment provided within the capsule and wherein an air curtain separates the two independently controllable chambers to maintain the selected environment within at least one of the chambers wherein the air curtain comprises a directed air flow.

7. The capsule of claim 6, wherein the two independently controllable chambers comprise a first chamber and a second chamber, wherein the first chamber is a portion of the capsule configured to surround a torso and legs portion of the human patient and the second chamber is a portion of the capsule configured to surround a head and neck portion of the human patient and air knives provide the air curtain separating the first chamber and second chamber.

8. The capsule of claim 6, wherein at least one of the independently controllable chambers comprise a heating mechanism for controlling the temperature within the at least one chamber.

9. The capsule of claim 8, wherein the heating mechanism is a convection heating system for providing dry heat to the at least one chamber through one or more ports in the capsule.

10. The capsule of claim 8, wherein the heating mechanism is an infrared heating system providing heat to the at least one chamber through a panel of infrared emitters in the capsule.

11. The capsule of claim 6, wherein at least one of the independently controllable chambers comprises a cooling fan for directing cooled air into the at least one chamber for controlling the temperature of the chamber.

12. The capsule of claim 6, the capsule further comprising an intake port for providing pure oxygen to at least one of the independently controllable chambers.

13. The capsule of claim 6, wherein the physical exercise equipment pieces comprise one or more selected from the group consisting of exercise resistance bands, stack weights coupled to hand or foot grips, a push pedal stepper, stationary cycle, hand stirrups for isometric exercises, and the pull-up bar.

14. A method of hyperthermic conditioning comprising:
providing a capsule comprising a base and a cover forming a temperature controlled personal compartment therein and a removable hood, the cover being hingedly connected to the base and a removable pull up bar attached to the base and configured for use when the cover is removed;
controlling a temperature of the personal compartment with one or more heating elements configured to elevate the temperature within the personal compartment;
providing one or more pieces of physical exercise equipment within the personal compartment for hyperthermic conditioning wherein at least one of the one or more pieces of physical exercise equipment are operably secured to a bed portion of the capsule wherein the bed portion is secured to the base portion and is transparent to lights of different wavelengths and wherein surfaces of the bed portion are positioned at various angles such that the bed portion comprises an upper body portion, a lower back portion and a leg panel;
wherein the capsule supports one or more of a LED light panel, infrared light panel, a source of heated air, a source of cooled air, a showerhead, and a steam outlet for further controlling an environment within the personal compartment; and
wherein the capsule has dimensions sufficiently large to allow a user to move within the personal compartment when utilizing the one or more pieces of physical exercise equipment secured to the bed.

15. The method of claim 14, wherein the one or more pieces of physical exercise equipment comprise one or more of resistance bands, a push-pedal stepper, and weights.

16. The method of claim 14 and further comprising:
removing the cover;
directing air flow across an upper portion of the personal compartment for substantially maintaining the temperature within the personal compartment;
providing one or more pieces of physical exercise equipment selected from the group consisting of a pull-up bar, stretching bands, cords, free weights, or wrist or ankle weights.

17. The method of claim 14 and further selecting the environment within the personal compartment by activating one or more of a cooling air fan, a pure oxygen flow, salt blocks, and LED lights.

* * * * *